United States Patent [19]

Gordon et al.

[11] Patent Number: 4,457,933
[45] Date of Patent: Jul. 3, 1984

[54] PREVENTION OF ANALGESIC ABUSE

[75] Inventors: Maxwell Gordon, Syracuse; Irwin J. Pachter; Fayetteville, both of N.Y.

[73] Assignee: Bristol-Myers Company, New York, N.Y.

[21] Appl. No.: 329,839

[22] Filed: Dec. 11, 1981

Related U.S. Application Data

[63] Continuation-in-part of Ser. No. 114,786, Jan. 24, 1980, abandoned, which is a continuation-in-part of Ser. No. 962,868, Nov. 24, 1978, abandoned.

[51] Int. Cl.³ .................... A01N 43/42; A61K 9/10; A61K 9/20
[52] U.S. Cl. .................................. 424/260; 424/14; 424/21; 424/32; 424/168; 424/170; 424/357
[58] Field of Search ........................................ 424/260

[56] References Cited

U.S. PATENT DOCUMENTS

| | | | |
|---|---|---|---|
| 3,254,088 | 5/1966 | Lewenstein | 424/260 |
| 3,466,277 | 9/1969 | Merz et al. | 260/240 |
| 3,493,657 | 2/1970 | Lewenstein | 424/260 |
| 3,676,557 | 7/1972 | Lachman et al. | 424/260 |
| 3,773,955 | 11/1973 | Pachter | 424/260 |
| 4,126,684 | 11/1978 | Robson et al. | 424/254 |

OTHER PUBLICATIONS

Modern Drug Encyclopedia & Therapeutic Index, 8, 1975, pp. 550–551.
Hospital Formulary, vol. I, 1966, Sec. 28:08, Analgesics & Antipyretics.

*Primary Examiner*—Dale R. Ore
*Attorney, Agent, or Firm*—Richard R. Lloyd

[57] ABSTRACT

This invention concerns a method for decreasing both the oral and parenteral abuse potential of strong analgetic agents such as oxycodone, propoxyphene and pentazocine by combining an analgesic dose of the analgetic agents with naloxone in specific, relatively narrow ranges. Oxycodone-naloxone compositions having a ratio of 2.5–5:1 parts by weight and pentazocine-naloxone compositions having a ratio of 16–50:1 parts by weight are preferred.

11 Claims, No Drawings

PREVENTION OF ANALGESIC ABUSE

CROSS-REFERENCE TO RELATED APPLICATIONS

This application is a continuation-in-part of our prior, co-pending application Ser. No. 114,786, filed Jan. 24, 1980, now abandoned which in turn was a continuation-in-part of our prior, co-pending application Ser. No. 962,868, filed Nov. 24, 1978, now abandoned.

SUMMARY OF THE INVENTION

The potential for abuse, by both the oral and parenteral routes, of strong analgetic agents such as oxycodone, propoxyphene and pentazocine, is greatly decreased by combining an effective analgesic dose thereof with naloxone in specific, relatively narrow ranges of ratios by weight.

BACKGROUND OF THE INVENTION

It is known that strong analgetic agents such as oxycodone, propoxyphene or pentazocine can cause physical and psychic (mental) dependence in laboratory animals and man. This potential for abuse restricts the use of these agents as analgetics to a considerable extent. The present invention is concerned with a method of decreasing both the oral and parenteral abuse potential of strong analgetic agents, such as oxycodone, propoxyphene or pentazocine, by administration of the analgetic agent in combination with naloxone, thereby permitting more extensive analgesic use.

DESCRIPTION OF THE PRIOR ART

U.S. Pat. No. 3,773,955 issued Nov. 20, 1973 to I. J. Pachter and M. Gordon describes orally effective analgetic compositions which, upon parenteral administration, do not produce analgesia, euphoria or physical dependence, and thereby prevent parenteral abuse of the analgetic agents. Examples of such compositions, in parts by weight, include 1 part of naloxone per 2 to 20 parts of oxycodone, 1 part of naloxone per 12 to 120 parts of dextropropoxyphene (propoxyphene) and 1 part of naloxone per 8 to 80 parts of pentazocine. Reference is also made to oral unit dosage forms of analgesics containing from 0.1 mg to about 10 mg of naloxone per analgetic oral dose. This reference is not concerned with the prevention of oral abuse of analgetic agents.

U.S. Pat. No. 3,493,657 issued Feb. 3, 1970 to M. J. Lewenstein et al. discloses compositions comprising a mixture of naloxone (i.e., N-allyl-14-hydroxydihydronormorphinone) and morphine or oxymorphone (i.e., 14-hydroxydihydronormorphinone). Such compositions are said to provide a strong analgesic effect without occurrence of undesired or dangerous side effects such as confusion, dream states, frightening experiences (i.e., hallucinations), etc. This reference does not disclose oxycodone, propoxyphene or pentazocine, not is it concerned with preventing parenteral and/or oral abuse of any type of drug.

DETAILED DESCRIPTION OF THE INVENTION

The prior art teaches combinations of strong analgetic agents with naloxone which are effective in producing analgesia when administered orally as intended, but which cannot be parenterally abused by addicts or "thrill seekers". This is due to the fact that, upon parenteral administration of the combination, the naloxone negates the effect of the strong analgetic agent and prevents the desired "high". However, the prior art does not address itself to the oral abuse of strong analgetic agents.

This invention is concerned with the discovery that the combination of strong analgetic agents such as oxycodone, propoxyphene and pentazocine with naloxone in relatively specific ratios decreases the potential not only for parenteral abuse of the strong analgetic agent but also its oral abuse. When utilized in the combinations of the present invention, both the oral and parenteral abuse potentials of strong analgetic agents are substantially diminished without appreciably affecting the oral analgetic activity of these agents. As a result of the reduced abuse potential, the present invention provides a means whereby certain strong analgetic agents in combination with naloxone may be subject to a lower schedule of narcotic control than required of the analgetic agent alone, thereby permitting greater use thereof.

In a preferred embodiment, this invention relates to a method for decreasing the potential for either oral or parenteral use of a strong analgetic agent as a hallucinogen or for satisfaction of a physical or psychic dependence thereon, which comprises administering to a human an orally effective analgesic dose of an analgetic agent selected from oxycodone, propoxyphene, pentazocine, methadone, tilidine, butorphanol, buprenorphine, levorphanol, codeine, oxymorphone, hydromorphone, meperidine, dihydrocodeinone and l-α-acetylmethadol, in combination with an amount of naloxone sufficient to substantially eliminate the possibility of either oral or parenteral abuse of said analgetic agent without substantially affecting the oral analgesic activity thereof.

Set forth below are a number of generally used strong analgetic agents, the ratio of analgetic agent to naloxone which is useful to prevent both oral and parenteral abuse of each analgetic agent, the usual oral analgesic unit dosage of each analgetic agent and the usual amount of naloxone to be combined with the stated unit dosage of each analgetic agent. In some instances a range of dosages is shown for an analgetic agent. The actual dosage of analgetic agent to be administered is, of course, within the discretion of the physician.

| Analgetic Agent | Ratio of Analgetic Agent to Naloxone | Usual Oral Unit Dosage of Analgetic Agent | Usual Amount of Naloxone per Stated Unit Dosage |
|---|---|---|---|
| oxycodone | 2.5:1 to 5:1 | 5–7.5 mg | 1–3 mg |
| propoxyphene | 32:1 to 65:1 | 32–130 mg | 1–4 mg |
| pentazocine | 16:1 to 50:1 | 50 mg | 1–3 mg |
| methadone | 1.67:1 to 5:1 | 5 mg | 1–3 mg |
| tilidine | 25:1 to 75:1 | 75 mg | 1–3 mg |
| butorphanol | 2.67:1 to 8:1 | 8 mg | 1–3 mg |
| buprenorphine | 0.67:1 to 2:1 | 2 mg | 1–3 mg |
| levorphanol | 0.67:1 to 2:1 | 2 mg | 1–3 mg |
| codeine | 10:1 to 30:1 | 30 mg | 1–3 mg |
| oxymorphone | 0.67:1 to 2:1 | 2 mg | 1–3 mg |
| hydromorphone | 0.67:1 to 2:1 | 2 mg | 1–3 mg |
| meperidine | 16:1 to 50:1 | 50 mg | 1–3 mg |
| dihydrocodeinone | 3.3:1 to 10:1 | 10 mg | 1–3 mg |
| l-α-acetylmethadol* | 1:1 to 5:1 | 5–100 mg | 1–20 mg |

*For addict maintenance

A more preferred embodiment of the present invention is a method for decreasing the potential for both oral and parenteral abuse of oxycodone comprising administering to a human an analgesic dose thereof as an oxycodone-naloxone composition having the ratio of 2.5–5:1 parts by weight wherein said composition contains from 1 to 3 mg of naloxone.

Another more preferred embodiment is a method for decreasing the potential for both oral and parenteral abuse of oxycodone comprising administering to a human an analgesic dose thereof as an oxycodone-naloxone composition having a ratio of 2.5–5:1 parts by weight wherein said composition contains from 1.4 to 2.5 mg of naloxone.

Another more preferred embodiment is a method for decreasing the potential for both oral and parenteral abuse of oxycodone comprising administering to a human an analgesic dose thereof as an oxycodone-naloxone composition having a ratio of 3–4:1 parts by weight wherein said composition contains from 1 to 3 mg of naloxone.

Another more preferred embodiment is a method for decreasing the potential for both oral and parenteral abuse of oxycodone comprising administering to a human an analgesic dose thereof as an oxycodone-naloxone composition having a ratio of 3.5:1 parts by weight wherein said composition contains from 1 to 3 mg of naloxone.

Another more preferred embodiment is a method for decreasing the potential for both oral and parenteral abuse of oxycodone comprising administering to a human an analgesic dose thereof as an oxycodone-naloxone composition having a ratio of 3.5:1 parts by weight wherein said composition contains from 1.4 to 2.5 mg of naloxone.

Another more preferred embodiment is a method for decreasing the potential for both oral and parenteral abuse of oxycodone comprising administering to a human an analgesic dose thereof as an oxycodone-naloxone composition containing from 2.5 to 10 mg of oxycodone and from 1 to 3 mg of naloxone.

In another aspect of this invention a more preferred embodiment is a method of decreasing the potential for both oral and parenteral abuse of pentazocine comprising administering to a human an analgesic dose thereof as a pentazocine-naloxone composition having a ratio of 16–50:1 parts by weight wherein said composition contains from 1 to 3 mg of naloxone.

Another more preferred embodiment of this invention is a method of decreasing the potential for both oral and parenteral abuse of pentazocine comprising administering to a human an analgesic dose thereof as a pentazocine-naloxone composition having a ratio of 16–50:1 parts by weight wherein said composition contains from 1.4 to 2.5 mgs of naloxone.

Another more preferred embodiment of this invention is a method of decreasing the potential for both oral and parenteral abuse of pentazocine comprising administering to a human an analgesic dose thereof as a pentazocine-naloxone composition having a ratio of 20–40:1 parts by weight wherein said composition contains from 1 to 3 mgs of naloxone.

Another more preferred embodiment of this invention is a method of decreasing the potential for both oral and parenteral abuse of pentazocine comprising administering to a human an analgesic dose thereof as a pentazocine-naloxone composition having a ratio of 25:1 parts by weight wherein said composition contains from 1.4–2.5 mgs of naloxone.

Another more preferred embodiment of this invention is a method of decreasing the potential for both oral and parenteral abuse of pentazocine comprising administering to a human an analgesic dose thereof as a pentazocine-naloxone composition containing from 25 to 100 mg of pentazocine and from 1 to 3 mg of naloxone.

Pharmaceutical compositions containing from 2.5 to 15 mg of oxycodone and from 1 to 3 mg of naloxone can be formulated according to conventional pharmaceutical practice to provide unit dosage forms which may include solid preparations suitable for oral administration such as tablets, capsules, powders, granules, emulsions and suspensions, as well as liquid preparations suitable for parenteral administration. For instance, the solid preparations of oxycodone-naloxone are prepared with an inorganic carrier, e.g., talc, or an organic carrier such as lactose or starch while liquid preparations suitable for parenteral administration are prepared with the usual diluent such as water, or suspension media such as petroleum jelly, polyoxyethyleneglycol, vegetable oils and the like. The compositions may also include other additional ingredients such as absorbing agents, stabilizing agents and buffers. A particularly preferred composition contains from 2.5 to 10 mg of oxycodone and from 1 to 3 mg of naloxone. Pharmaceutical compositions containing from 32 to 260 mg of propoxyphene and from 1 to 4 mg of naloxone are formulated by conventional means as described above. A particularly preferred composition contains from 32 to 130 mg of propoxyphene and from 1 to 4 mg of naloxone. Compositions of other strong analgetic agents and naloxone are formulated in the same manner as described above and in ratios set forth above for each analgetic agent.

The compositions of the present invention comprised of 2.5–5:1 parts by weight of oxycodone-naloxone, 32–65:1 parts by weight of propoxyphene-naloxone and 16–50:1 parts by weight of pentazocine-naloxone are almost indistinguishable from oxycodone, propoxyphene or pentazocine, respectively, with respect to oral analgetic activity in animals. Such mixtures do not suppress abstinence in morphine-dependent monkeys and have low physical dependence capacity in direct addiction experiments. For instance, oxycodone administered orally to monkeys was classified as possessing high physical dependence liability whereas a mixture of oxycodone-naloxone at a ratio of 3.5:1 was classified as having low physical dependence liability.

The following examples which serve to illustrate but do not limit the invention describe several animal experiments confirming the analgesic activity and the decrease in abuse potential of the oxycodone-naloxone mixtures in addition to the analgesic activity of the instant propoxyphene-naloxone compositions.

EXAMPLE 1

Abstinence Suppression in Morphine-Dependent Monkeys

Morphine dependence was induced in male rhesus monkeys by daily subcutaneous injections of morphine. The initial dose of 7.5 mg/kg body weight was gradually increased at 14-day intervals to a final maintenance dose of 60 mg/kg. Physical dependence was indicated by abstinence signs which appeared gradually after 48 hours following withdrawal of morphine. These signs included piloerection, adoption of unusual postures, increased vocalization, bared teeth, tremor, exaggerated response to observer approach, sweating, prostration and dyspnoea, all of which could be suppressed by a subcutaneous dose of 3 mg/kg of morphine. Mixtures of oxycodone-naloxone were administered 48 hours after withdrawal from morphine, when the abstinence signs were usually of moderate intensity, and compared with oxycodone. Results are shown in Table 1 below.

TABLE 1

| Oxycodone-Naloxone Ratio | Abstinence Suppression Dose of Oxycodone* | |
|---|---|---|
| | 40 mg/kg | 160 mg/kg |
| 1:0 | Moderate | Complete |
| 10:1 | — | Complete |
| 5:1 | None | Moderate to complete |
| 3.5:1 | — | Initial exacerbation followed by mild suppression of generally short duration. |

*Dose of test material expressed in terms of oxycodone hydrochloride content.

This study illustrates that a ratio of 3.5:1 oxycodone-naloxone has a relatively low order of narcotic-like abuse liability since it does not suppress the opiate withdrawal syndrome to any large degree.

EXAMPLE 2

Physical Dependence Capacity (Direct Addiction) in Monkeys

Oxycodone or a mixture of oxycodone-naloxone in a ratio of 3.5:1 was administered orally by gavage, twice daily for a period of 40 days to four naive monkeys according to the following schedule in which all doses of oxycodone are expressed in terms of the base and the stated doses of the mixture refer to the content of oxycodone.

| Days | Dose of Oxycodone in the Oxycodone/Naloxone Mixture (mg/kg × 2) | Dose of Oxycodone (mg/kg × 2) |
|---|---|---|
| 1–10 | 90 | 90 |
| 11–20 | 180 | 120 |
| 21–30 | 240 | 220 |
| 31–40 | 300 | 300 |

After 35 days, four hours after the morning dose of mixture of oxycodone, each animal received a subcutaneous injection of 100 microgram per kg naloxone hydrochloride. The monkeys were then observed continuously for the next 60 minutes for the rapid development of withdrawal signs which might be precipitated by the naloxone. Further observations were made at ½ hour intervals until 2½ hours after naloxone administration. Dosing with mixture or oxycodone was then continued up to the 40th day and thereafter the monkeys were observed intermittently for 7 days for the appearance of withdrawal signs. The following results were seen.

Naloxone challenge on 35th day:
Oxycodone alone:
  Precipitation of severe withdrawal signs lasting longer than 3 hours
Oxycodone/Naloxone:
  ¼ no withdrawal signs
  2/4 mild withdrawal signs
  ¼ mild to moderate withdrawal signs.
Withdrawal of medication at the 40th day:
Oxycodone alone:
  Precipitation of quite marked withdrawal signs lasting longer than the seven-day observation period
Oxycodone/Naloxone:
  2/4 no evidence of any withdrawal signs
  ¼ possibly very mild withdrawal signs
  ¼ very mild withdrawal, not evident after 4 days.

According to the above results, oxycodone was classified as possessing high physical dependence liability, whereas an oxycodone-naloxone mixture at a ratio of 3.5:1 was classified as possessing low physical dependence liability.

EXAMPLE 3

Oxycodone-Naloxone Analgesic Response In Rats

The dose of naloxone administered in combination with oxycodone, which does not affect the analgesic activity of oxycodone, was determined according to the radiant heat method of D'Amour and Smith, J. Pharmacol. Exp. Therap., 72: 74, (1941) performed in rats. In this method, the end point employed for analgesia was the tail flick determined at 30, 60 and 120 minutes after oral or subcutaneous dosing. The analgesic $ED_{100}$ was defined as that dose which produced 100% increase in the individual predose response time in 100% of the animals at any one of the test intervals. Blockade of analgesia was considered evident when a dose of concomitantly administered naloxone reduced individual analgesic response below a 100% increase in response time. The following results were obtained.

| | Analgesic $ED_{100}$ for Oxycodone (mg/kg) | Antagonistic $AD_0$ for Naloxone (mg/kg)* | Ratio Analgesic $ED_{100}$/ Antagonistic $AD_0$ |
|---|---|---|---|
| Subcutaneously | 2.5 | 0.008 | 313 |
| Orally | 15.5 | 5.7 | 2.7 |

*That dose of naloxone, administered in conjunction with the $ED_{100}$ dose of oxycodone, at which 100 percent of the animals still demonstrated a 100 percent increase in the predose response time (analgesic effect).

EXAMPLE 4

Oxycodone-Naloxone Analgesic Response in Mice

The dose of naloxone administered in combination with oxycodone, which does not affect the analgesic activity of oxycodone was determined according to the mouse phenylquinone induced writhing test of Siegmund et al., Proc. Soc. Exp. Biol. and Med., 95: 729, (1957). In this method the end point employed for analgesia was taken as absence of the writhing response over a 10 minute period beginning 5 minutes after the intraperitoneal administration of phenylquinone. The $ED_{95}$ was defined as that dose which protected greater than 95% of the mice 30 minutes after oral administration of the test agent. Blockage of analgesia was considered evident when a dose of concomitantly administered naloxone resulted in the writhing response. The following results were obtained.

| | Analgesic $ED_{95}$ for Oxycodone (mg/kg) | Antagonistic $AD_0$ for Naloxone (mg/kg)* | Ratio Analgesic $ED_{95}$/ Antagonistic $AD_0$ |
|---|---|---|---|
| Subcutaneously | 1.3 | 0.003 | 433 |
| Orally | 2.6 | 1.0 | 2.6 |

*That dose of naloxone, administered in conjunction with the $ED_{95}$ dose of oxycodone, at which the writhing response was still absent in >95 percent of the mice (analgesic effect).

EXAMPLE 5

Propoxyphene-Naloxone Analgesic Response in Rats

The dose of naloxone administered in combination with propoxyphene, which does not effect the analgesic activity of propoxyphene was determined in rats according to the radiant heat method of Example 3 with the following results.

|  | Analgesic $ED_{100}$ for Propoxyphene (mg/kg) | Antagonistic ADo for Naloxone (mg/kg)* | Ratio Analgesic $ED_{100}$/ Antagonistic ADo |
|---|---|---|---|
| Subcutaneously | 28.4 | 0.005 | 5,680 |
| Orally | 80.0 | 3.0 | 26.7 |

*That dose of naloxone, administered in conjunction with the $ED_{100}$ dose of propoxyphene, at which 100 percent of the animals still demonstrated a 100 percent increase in the predose response time (analgesic effect).

EXAMPLE 6

Propoxy-Naloxone Analgesic Response in Mice

The dose of propoxyphene, administered in combination with oxycodone, which does not affect the analgesic activity of propoxyphene, was determined in mice according to the phenylquinone writhing test of Example 4 with the following results.

|  | Analgesic $ED_{95}$ for Propoxyphene (mg/kg) | Antagonistic ADo for Naloxone (mg/kg)* | Ratio Analgesic $ED_{95}$/ Antagonistic ADo |
|---|---|---|---|
| Subcutaneously | 20 | 0.018 | 1,111.1 |
| Orally | 102 | 5.0 | 20.4 |

*That dose of naloxone, administered in conjunction with the $ED_{95}$ dose of propoxyphene, at which the writhing response was still absent in >95 percent of the mice (analgesic effect).

We claim:

1. A method for decreasing the potential for oral abuse of an analgesic dose of oxycodone orally administered to a human comprising orally administering an oxycodone-naloxone composition having a ratio of 2.5–5:1 parts by weight wherein said composition contains from 1 to 3 mg of naloxone.

2. The method of claim 1 wherein the oxycodone-naloxone composition contains from 1.4 to 2.5 mg of naloxone.

3. The method of claim 1 wherein the oxycodone-naloxone composition has a ratio of 3:1 to 4:1 parts by weight.

4. The method of claim 1 wherein the oxycodone-naloxone composition has a ratio of 3.5:1 parts by weight.

5. The method of claim 1 wherein the oxycodone-naloxone composition has a ratio of 3.5:1 parts by weight and contains from 1.4 to 2.5 mg of naloxone.

6. The method of claim 1 wherein the oxycodone-naloxone composition contains from 2.5 to 10 mg of oxycodone and from 1 to 3 mg of naloxone.

7. A method for decreasing the potential for oral abuse of an analgesic dose of pentazocine orally administered to a human comprising orally administering a pentazocine-naloxone composition having a ratio of 16–50:1 parts by weight wherein said composition contains from 1 to 3 mg of naloxone.

8. The method of claim 7 wherein the pentazocine-naloxone composition contains from 1.4 to 2.5 mg of naloxone.

9. The method of claim 7 wherein the pentazocine-naloxone composition has a ratio of 20–40:1 parts by weight.

10. The method of claim 7 wherein the pentazocine-naloxone composition has a ratio of 25:1 parts by weight and contains from 1.4 to 2.5 mg of naloxone.

11. The method of claim 7 wherein the pentazocine-naloxone composition contains from 25–100 mg of pentazocine and from 1 to 3 mg of naloxone.

* * * * *